United States Patent
Mouchawar et al.

(10) Patent No.: US 6,363,280 B1
(45) Date of Patent: Mar. 26, 2002

(54) BATTERY CONSERVATION IN IMPLANTABLE CARDIOVERTER-DEFIBRILLATORS AND PACEMAKERS

(75) Inventors: Gabriel Mouchawar, Newhall; James D. Causey, III, Simi Valley, both of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/418,925

(22) Filed: Oct. 15, 1999

(51) Int. Cl.$^7$ ............................................. A61N 1/362
(52) U.S. Cl. ............................. 607/16; 607/4; 607/14
(58) Field of Search .............................. 607/4, 5, 9, 14, 607/16

(56) References Cited

U.S. PATENT DOCUMENTS

| | | |
|---|---|---|
| 4,398,536 A | 8/1983 | Nappholz et al. |
| 4,427,011 A | 1/1984 | Spurrell et al. |
| 4,541,430 A | 9/1985 | Elmqvist et al. |
| 4,712,555 A | 12/1987 | Thornander et al. |
| 4,788,980 A | 12/1988 | Mann et al. |
| 4,809,697 A | 3/1989 | Causey, III et al. |
| 4,940,052 A | 7/1990 | Mann et al. |
| 4,944,298 A | 7/1990 | Sholder |
| 4,944,299 A | 7/1990 | Silvian |
| 5,103,822 A | 4/1992 | Duncan |
| 6,038,476 A | * 3/2000 | Schwartz ..................... 607/27 |
| 6,157,859 A | * 12/2000 | Alt ................................. 607/4 |

* cited by examiner

*Primary Examiner*—George R. Evanisko
*Assistant Examiner*—John Bird (57) ABSTRACT

In an implantable cardioverter-defibrillator and/or pacemaker, each having DDD pacing capabilities, an improved method of operation is described which dramatically increases the longevity of the implanted device by conserving battery power. The method comprises deactivating at least one unnecessary, power-consuming feature of the device until such feature is needed and then reactivating said feature only for so long as it is required by the patient. In a particular embodiment, the atrial sense amplifier is deactivated during normal operation of the implantable device, resulting in single-chamber sensing and pacing. Upon the occurrence of a predefined event, indicative of a need for dual-chamber sensing and pacing, the atrial sense amplifier is reactivated, the need for DDD pacing confirmed, and if appropriate, DDD pacing is begun. Once the patient's heart rate has returned to an acceptable level, the atrial sense amplifier is again deactivated and single-chamber sensing/pacing continued. In addition, the atrial sense amplifier of an ICD/pacemaker is deactivated during normal operation of the device and reactivated immediately following the detection of ventricular tachycardia. In this embodiment, DDD sensing/pacing is preferably automatically begun following this detection. Also contemplated herein, are improved devices employing the improved methods.

4 Claims, 4 Drawing Sheets

BATTERY CONSERVATION IN IMPLANTABLE CARDIOVERTER-DEFIBRILLATORS AND PACEMAKERS

FIELD OF THE INVENTION

The subject matter disclosed and claimed herein relates to an improved method of operation of pacemakers and implantable cardioverter-defibrillators (ICDs) having pacing capabilities, which improved method serves to prolong battery longevity by deactivating certain power-consuming features while not needed and reactivating as necessary. Also provided herein are improved devices employing these methods.

BACKGROUND OF THE INVENTION

The heart functions to pump life-sustaining blood throughout one's body. The human heart comprises a left side and a right side with each side having a first chamber known as the atrium and a second chamber known as the ventricle. The right atrium receives blood from the body after the body has extracted the oxygen therefrom and the left atrium receives oxygenated blood from the lungs. At an appropriate time, an electrical stimulus is provided to the atria that causes the muscle tissue to depolarize. Immediately following depolarization, the atrial muscle tissue physically contracts, forcing the blood held in the right and left atria through one-way valves into the right and left ventricles, respectively.

The electrical stimulus provided to the atria also stimulates the ventricles after a delay which is sometimes referred to as the "natural conduction time" of the heart. Upon stimulation, the ventricular muscle tissue depolarizes and then contracts. This forces the blood held within the right ventricle to pass through the pulmonary artery to the lungs and the blood held within the left ventricle to pass through the aorta to the rest of the body. In this manner, then, the heart "beats" or pumps blood by having the atria contract and, after the natural conduction time, by having the ventricles contract. After a longer delay, during which delay the right atrium is refilled with blood returning from throughout the body, the process repeats.

Implantable pacemakers and cardioverter-defibrillators (ICDs) are electronic medical devices that monitor the electrical activity of the heart and provide electrical stimulation to one or more heart chambers, when necessary. For example, a pacemaker senses an arrhythmia, i.e., a disturbance in heart rhythm, and provides appropriate electrical stimulation pulses, at a controlled rate, to selected chambers of the heart in order to correct the arrhythmia and restore the proper heart rhythm. The type of arrhythmias that may be detected and corrected by pacemakers include bradycardias, which are unusually slow heart rates, and certain tachycardias, which are unusually fast heart rates.

Implantable cardioverter-defibrillators (ICDs) also detect arrhythmias and provide appropriate electrical stimulation pulses to selected chambers of the heart to correct the abnormal heart rate. In contrast to pacemakers, however, the pulses from an ICD are much stronger and less frequent. This is because ICDs are generally designed to correct fibrillations, which are rapid, unsynchronized quiverings of one or more heart chambers, and severe tachycardias, where the heart beats are very fast but coordinated. To correct such arrhythmias, an ICD delivers a low, moderate or high energy shock to the heart. In addition to functioning as a cardioverter-defibrillator, some ICDs are designed to provide pacing support to the heart. Such ICDs sense the occurrence of a cardiac arrhythmia and automatically apply an appropriate therapy to the heart aimed at terminating the specific arrhythmia detected. This type of therapy is referred to as "tiered therapy".

In a tiered therapy ICD, each "tier" or level of therapy generally corresponds to a different type of arrhythmia and typically to a specified number of shocks of varying energies and pulse durations intended to most efficiently terminate the specific type of arrhythmia detected. Thus, such tiered therapy may include antitachycardia pacing for painless termination of monomorphic ventricular tachycardia (i.e., tachycardia that originates from one ventricular focus); programmable low-energy cardioversion also for treatment of ventricular tachycardia (e.g., when antitachycardia pacing fails to terminate the tachycardia); high-energy defibrillation for termination of ventricular fibrillation; and back-up bradycardia pacing, for ensuring the heart beats, particularly following cardioversion or defibrillation. For examples of tiered therapy ICDs, see U.S. Pat. Nos. 4,427,011; 4,541,430; 4,398,536; and 5,103,822; each of which is incorporated herein, in its entirety, by reference.

Because the invention described and claimed herein is useful in pacemakers, ICDs and tiered therapy ICDs, these devices will be collectively referred to as "ICD/pacemakers". It will be appreciated by those of skill in the art that discussions herein of the pacing functions of an implantable device generally refer only to pacemakers and/or ICDs having pacing capabilities, whereas discussions of cardioverting-defibrillating functions generally only refer to ICDs with or without pacing capabilities.

The pacing functions of ICD/pacemakers are described as either single-chamber or dual-chamber systems. A single-chamber ICD stimulates and senses the ventricular chamber of the heart. A dual-chamber system stimulates and/or senses in two chambers of the heart (an atrium and a ventricle). Dual-chamber systems may typically be programmed to operate in either a dual-chamber mode or a single-chamber mode.

A three-letter code (sometimes expanded to a five letter code) is used to describe the basic mode in which the ICD/pacemaker is operating. The three-letter code concerns how the device operates to sense the need for and provide electrical stimulation to the heart. A fourth position (when used) identifies the degree of programmability and rate modulation of the device, and a fifth position (when used) refers to electrical stimulation therapy for the primary treatment of tachycardias and fibrillations.

The first position of the three letter pacemaker code identifies the chamber to which the electrical stimulus is delivered. If the device is not capable of bradycardia support pacing, an "O" occupies this first position. If the unit paces in the ventricle, this is identified by a "V"; if it paces in the atrium, the first position is identified as an "A". If stimuli can be delivered to either the atrium or ventricle, the letter "D" is used to reflect dualchamber stimulation.

The second position of the pacemaker code identifies the chamber or chambers in which sensing occurs. Sensing is the ability of the pacemaker to recognize the intrinsic electrical activity of the heart. The letters used in this position are identical to those used in the first position, i.e., "V" for ventricular sensing; "A" for atrial sensing; "D" for dual-chamber sensing; and "O" if no sensing capability is present.

The third position of the pacemaker code identifies the way the pacemaker responds to a sensed signal. An "I" means that the pacemaker will be inhibited. The inhibited mode of response indicates that when the pacemaker senses or sees an intrinsic electrical signal, it inhibits its own output pulse and resets one or more internal timers within the pacemaker's circuitry. The other basic response is represented by a "T", which means triggered. The triggered mode of response indicates that when the pacemaker senses an intrinsic electrical signal, it not only resets various internal timers within the pacemaker, it also initiates or releases a stimulus in response to that sensed event.

The most sophisticated response mode is represented by a "D" in the third position and refers to both modes of sensing response. Most commonly, a sensed signal arising from the atrium and sensed on the atrial channel of a dual-chamber pacemaker will inhibit the atrial output but trigger a ventricular output after a brief delay (the AV delay). If a native ventricular depolarization does not occur before the AV delay timer completes, a ventricular stimulus will be released at the end of this AV delay. If a native ventricular signal is sensed within the AV delay, the ventricular output will be inhibited and other timers will be reset. If a native ventricular signal is sensed before the atrial stimulus is released, both the atrial and ventricular output pulses will be inhibited and the various timers will be reset.

In order to perform their pacing and/or cardioverting-defibrillating functions, pacemaKers and ICDs must have an energy source, e.g., a battery. Because replacement of the battery requires explantation of the device and implantation of a new device, it is critical that the battery last as long as possible. A popular mode of operation for dual-chamber pacemakers, and, increasingly, ICDs having pacing capabilities, is the "DDD" mode. In this mode, the device provides electrical stimuli to both an atrium and a ventricle of the heart, senses electrical activity in both the atrium and ventricle and provides both inhibited and triggered responses to sensed electrical activity. Operating an ICD or pacemaker in the DDD mode consumes more battery energy than a mode of only single-chamber sensing and/or stimulation. For example, it is estimated that an ICD that also provides DDD pacing consumes roughly 20% more battery current than one that provides VVI pacing only. This translates into a reduction in longevity for the typical ICD of about one year.

ICD/pacemakers having DDD pacing capability are advantageous in that they are able to provide more appropriate therapy to the patient than such devices operating in, for example, VVI mode where stimulation and sensing occur only in the ventricle and the mode of response is only by inhibition of the pacing signal. Although VVI pacing may be usually sufficient for the patient, having DDD pacing available provides more complete therapy to the patient. Thus, what is needed are pacemakers and ICDs capable of providing DDD pacing without such a dramatic increase in energy consumption.

SUMMARY OF INVENTION

The subject matter disclosed and claimed herein advantageously addresses the above and other needs by providing an improved method of operation for ICD/pacemakers, which method provides for battery conservation in DDD pacing devices. Further provided herein are improved ICD/pacemakers employing the improved method.

Generally, the improved method provides for the deactivation of one or more power-consuming features of the implantable medical device during periods when those features are not critical or are not needed. For example, most ICD patients infrequently require pacing support. Further, when pacing support is required, it is usually needed only for a short time. Thus, in a most preferred embodiment, the improved method contemplates deactivation of the atrial sense amplifier during normal operation of an ICD, leaving active only the ventricular sense amplifier and pacing circuitry. Upon the occurrence of predefined events, for example excessive sequential ventricular pacing, the atrial sense amplifier is activated, and DDD pacing, if appropriate, is initiated. The atrial sense amplifier then remains activated until one or more predefined events occur, such as a return to a ventricular rate above the brady limit, at which point the atrial sense amplifier is again deactivated.

In an alternative embodiment, an improved method of operation of an ICD is contemplated, which method includes activation of the atrial sense amplifier and initiation of DDD pacing for a predefined period of time immediately following the administration of cardioversion and/or defibrillation therapy by the ICD. Since administration of cardioversion-defibrillation therapy can give rise to a bradycardia episode, this improved mode of operation is advantageous.

With respect to patients requiring only pacing support, rather than cardioversion-defibrillation and pacing, the improved method may be employed in DDD pacing pacemakers, thereby extending the useful life of those devices. For example, some pacemaker patients are amenable to single-chamber pacing support, but may benefit, from time to time, from dual-chamber pacing support. The general method is the same, that is, the atrial sensor remains deactivated until predefined cardiac events, sensed by the ventricular sense amplifier, suggest a need for dual-chamber pacing. At this point, the atrial sense amplifier is activated, and, if appropriate, a DDD mode of pacing is begun. Once the patient's heart rate has returned to within predefined acceptable limits, the atrial sense amplifier is again deactivated. As will be appreciated by those of skill in the art, an "acceptable heart rate" may be determined in numerous ways, for example, a return to a rate above the patient's brady limit or recordation of a substantial number of P-waves followed by R-waves are indicative of a stable heart rate that no longer requires DDD pacing. Similarly, examples of events that may be monitored for the purpose of determining when DDD pacing may be necessary include an excessive frequency of ventricular pacing and/or an excessive number of sequential ventricular pacing events. Thus, using the improved method described and claimed herein, these pacemaker patients may advantageously use their implanted device for a longer period of time.

Also provided herein are implantable ICDs and pacemakers employing these new methods to extend the useful lives thereof. In preferred embodiments, these devices include means for generating stimulation pulses; first sensing means for sensing electrical activation of the heart at the right and/or left ventricle; second sensing means for sensing electrical activation of the heart at the right and/or left atrium; activation/deactivation means, responsive to the first and/or second sensing means, for activating and deactivating the second sensing means and/or the means for generating stimulation pulses; microprocessor control and timing circuits; a clock; and a power source, such as a battery. In a most preferred embodiment, the implantable device further includes memory for storing information on the operation of the device as well as patient-specific information and data; and telemetry means for receiving/sending information and data from/to the memory and from/to an external programmer. Additionally, if the implantable device is an ICD, cardioverter-defibrillator circuitry is included.

Thus, it is a feature of the present invention to provide an implantable medical stimulating device, and method of operating such device, which conserves the limited energy of the device's battery.

It is a another feature of the invention to provide an implantable medical device that can operate in at least two modes, and wherein the device automatically operates in whichever mode consumes the least power, except when conditions require operation in another mode.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims. Provided herein is a method of operation of implantable cardioverter-defibrillators (ICDs) and/or pacemakers, which method prolongs the battery life of the implantable device by deactivating certain power-consuming features while not needed and reactivating those features as necessary. Also provided herein are improved devices employing these methods.

In one aspect, the method provided herein involves operating an ICD/pacemaker, having DDD pacing capabilities, with the atrial sense amplifier in a deactivated state until it is determined by the device that DDD pacing may be necessary. For example, in a particular embodiment, the activity of the ventricular pulse generator is monitored and the atrial sense amplifier activated when a predefined number of sequential ventricular pacing events have occurred and/or when ventricular pacing episodes have occurred with a predefined, excessive frequency. Once the atrial sense amplifier has been activated, both atrial and ventricular activity are monitored to determine whether DDD pacing is actually required. If it is confirmed that DDD pacing is needed, it is begun; if DDD pacing is not needed, then heart activity is monitored to verify proper AV synchrony and the sense amplifier is again deactivated. Thus, in this embodiment, the atrial sense amplifier remains inactive and the device effectively operates in a VVI mode until there is a specific indication that DDD pacing may be needed, thereby saving the energy normally expended by having the atrial sense amplifier activated at all times.

In addition to the improved method described herein, which may be employed alone or in conjunction with the embodiment just described, an embodiment is described for use in ICDs. In this embodiment, the atrial sense amplifier is not activated until either a cardioversion or defibrillation episode is detected by the device. When this occurs, the atrial sense amplifier is activated and DDD pacing and sensing is initiated in order to ensure the heart returns to an acceptable level of functioning. As will be appreciated by those of skill in the art, this particular embodiment is most appropriate for patients that do not require DDD pacing at times other than immediately following cardioversion-defibrillation therapy. For such patients, this alternative embodiment will be tremendously beneficial, as the longevity of the implanted ICD will be dramatically improved as compared to the presently used ICD devices employing full-time DDD pacing capabilities.

In a further preferred embodiment of the improved method described herein, the atrial sense amplifier of an ICD, having pacing capabilities, is activated under both of the previously described situations, that is, both when the frequency and/or number of ventricular pacings is excessive (i.e., greater than a predetermined amount) and following tachycardia episodes. If the event triggering activation of the atrial sense amplifier is a tachycardia episode, then initiation of DDD pacing/sensing is automatic. If, on the other hand, the triggering event is an excessive (i.e., greater than a predetermined amount) frequency of ventricular pacings or similar indication of the need for DDD pacing, then the atrial sense amplifier is activated. However, DDD pacing is preferably initiated only if there is no atrial activity sensed by the atrial sense amplifier or the PR delay (the time between the intrinsic P-wave and the intrinsic R-wave) is longer than a predefined threshold. Although the atrial sense amplifier will be activated more often under this most preferred method, the energy savings compared to an ICD/pacemaker operating with a full-time atrial sensor is still significant. Further, this energy savings is realized with little or no risk to the patient.

In another aspect, the present invention is directed to an improved ICD/pacemaker employing one or more of the improved methods. For example, as described in detail below, the implantable device includes a control circuit, which preferably is microprocessor-based, that receives information from a ventricular sense amplifier and an atrial sense amplifier, that controls the issuance of stimulation pulses from a ventricular pulse generator and/or atrial pulse generator and activates/deactivates the atrial sense amplifier based upon the information received from the ventricular sense amplifiers and/or the operation of the pulse generators. Additionally, where the implantable device has cardioverting-defibrillating capabilities, the control circuit may, and preferably does, control the activation/deactivation of the atrial sense amplifier based upon the operation of the cardioversion-defibrillation circuitry.

It will be appreciated by those of skill in the art that the present invention may be used with various types of implantable medical devices, including implantable cardioverter-defibrillators (ICDS) or implantable dual-chamber pacemakers or, most preferably, implantable cardioverter-defibrillators having dual-chamber pacing capabilities. To better understand the invention it will first be helpful to have an understanding of the basic functions performed by a typical implantable medical device with which the invention is used. To that end, reference is first made to FIG. 1, where there is shown a simplified functional block diagram of an ICD/pacemaker device 10 having dual-chamber pacing capabilities.

It is the primary function of an ICD device to sense the occurrence of an arrhythmia and to automatically apply an appropriate electrical shock therapy to the heart 12 in order to terminate the detected arrhythmia. Thus, the ICD/pacemaker 10 shown in FIG. 1, includes a microprocessor-based control and timing circuit 22 (hereinafter a "control/timing" circuit) that controls the atrial (A PACE) and ventricular (V PACE) pulse generating means 28 and 30, respectively, and controls the cardioversion-defibrillation circuitry 38 of the device. The cardioversion-defibrillation circuitry 38 generates output electrical stimulation pulses of moderate to high energy as necessary to cardiovert or defibrillate the patient's heart 12. Thus, for example, electrical pulses having energies of from 1 to 10 Joules (moderate) or 11 to 40 Joules (high), as controlled by the control/timing circuit 22 are delivered, as appropriate. Such moderate or high energy pulses are preferably applied to the patient's heart 12 through a lead 14 which includes shocking electrodes 19 and 21, typically placed in the superior vena cava (SVC) and the right ventricle. While only two shocking electrodes are shown in FIG. 1 in association with the cardioversion-defibrillation circuitry, it is to be understood that additional cardioversion-defibrillation leads and electrodes may be used as desired or needed in order to efficiently and effectively apply the shock treatment generated by the cardioversion-defibrillation circuitry 38 to the patient's heart 12.

Figure 1:
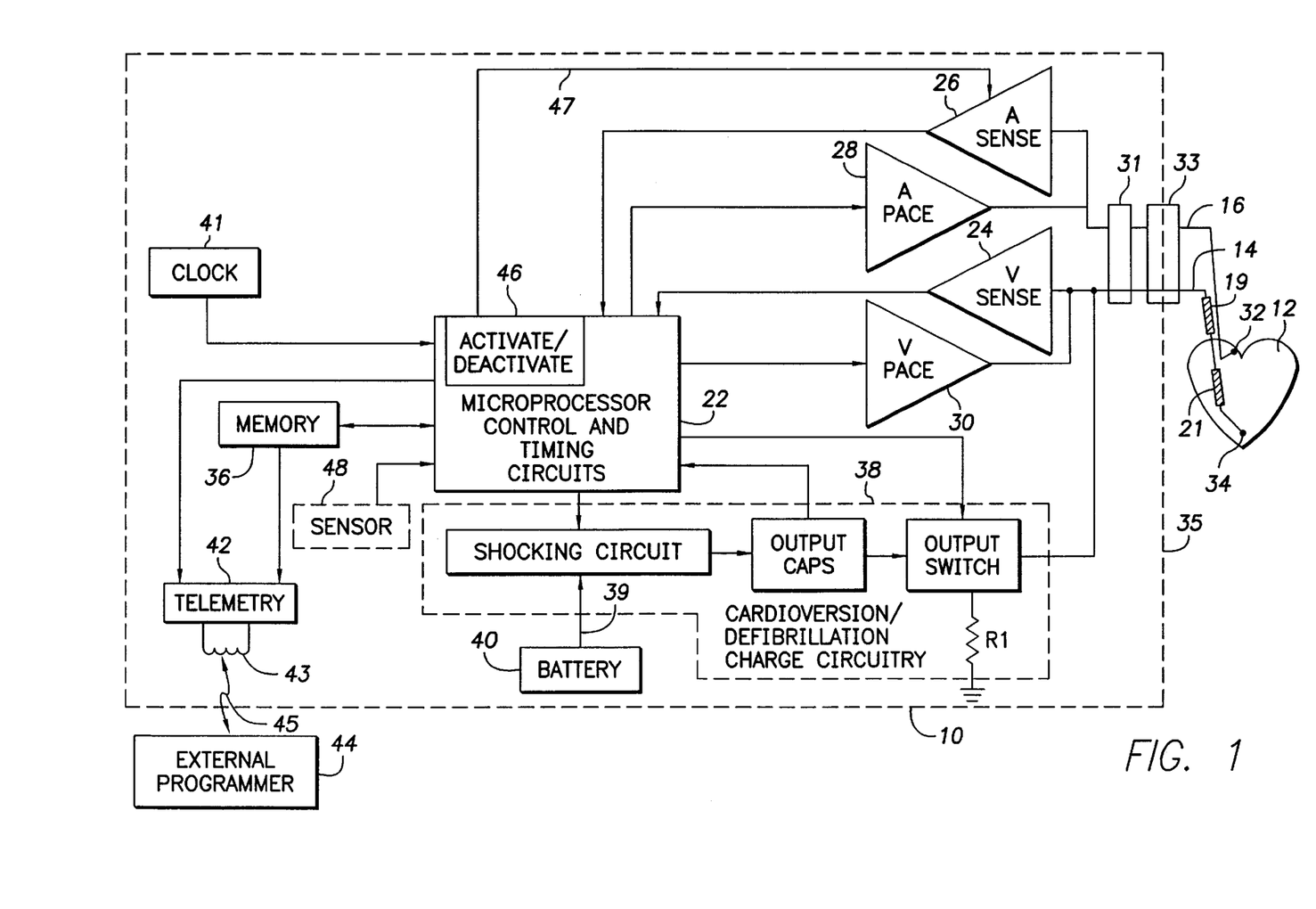
FIG. 1 is a block diagram of a representative microprocessor-based implantable cardioverter-defibrillator that may be used with the present invention.

Also illustrated in FIG. 1, there are two additional electrodes (an atrial electrode 32 and a ventricular electrode 34) coupling the ICD/pacemaker 10 to the heart 12. The ventricular electrode 34 is preferably formed at the distal end of lead 14 and is in contact with one of the ventricles of the heart 12 and an atrial lead 16 having an atrial electrode 32 is in contact with one of the atria of the heart 12. Leads 14 and 16 are electrically and physically connected to the ICD/pacemaker 10 through a connector 33 that forms an integral part of a housing 35, typically conductive, wherein the circuits of the ICD/pacemaker are housed. In the body of the ICD/pacemaker 10, and electrically connected to the connector, is a protection network 31 which electrically protects the circuits within the ICD/pacemaker 10 from excessive shocks or voltages that could appear on the electrodes 32, 34 in the event such electrodes were to come in contact with a high voltage signal, e.g., from a defibrillating shock.

The leads 14, 16 carry stimulating pulses to the electrodes 34, 32 from a ventricular pulse generator (V PACE) 30 and an atrial pulse generator (A PACE) 28, respectively. Further, electrical signals from the atria are carried from the electrode 32 through the lead 16 to the input terminal of an atrial sense amplifier (A SENSE) 26, and electrical signals from the ventricle are carried from the electrode 34 through the lead 14 to the input terminal of a ventricular sense amplifier (V SENSE) 24. It is the function of the sense amplifiers 26, 24 to sense the activity of the heart 12 as manifest by the presence of certain electrical signals sensed through the electrodes, 32 and 34, respectively. That is, as is known in the art, R-waves occur upon the depolarization, and hence contraction, of ventricular tissue; and P-waves occur upon the depolarization, and hence contraction, of atrial tissue. Thus, by sensing R-waves and/or P-waves through the ventricular 24 and/or atrial 26 sense amplifiers, respectively, and providing such sensed signals to the control/timing circuit 22, the control/timing circuit 22 is able to make a determination as to the rate and regularity of the patient's heart beat. Such information, in turn, allows the control/timing circuit 22 to determine whether the heart 12 of a patient is experiencing an arrhythmia.

The control/timing circuit 22 then generates trigger signals that are sent to the atrial pulse generator 28 and/or the ventricular pulse generator 30. These trigger signals are generated each time that a stimulation pulse is to be generated by the respective pulse generator 28 or 30. Similarly, where the arrhythmia detected by the control/timing circuit 22 is a severe tachycardia or a fibrillation, the control/timing circuit 22 generates trigger signals to the cardioversion-defibrillation circuitry 38 as required to administer cardioversion and/or defibrillation therapy.

The control/timing circuit 22 preferably has a memory circuit 36 coupled thereto wherein the operating parameters used by the control/timing circuit 22 are stored. This memory circuit 36 allows the operating parameters of the device to be programmably stored and modified as required in order to customize the ICD/pacemaker's operation to suit the needs of a particular patient. Further, data sensed during the operation of the ICD/pacemaker 10 may be stored/recorded in the memory 36 for later retrieval and analysis.

The memory 36 may take many forms and may be subdivided into many different memory blocks or sections (addresses) as needed to store desired data and control information. A feature of the present invention is the ability to store within the memory 36 of the device information pertaining to frequency and number of ventricular paces performed by the ICD/pacemaker 10 and/or pertaining to the administration of cardioverting and/or defibrillating therapy by the ICD/pacemaker 10.

Advantageously, in the preferred embodiments herein, the operating parameters of the implantable ICD/pacemaker 10 may be non-invasively programmed into the memory 36 through a telemetry circuit 42 in telecommunicative contact with an external programmer 44 by way of a suitable coupling coil 43. The coupling coil 43 may serve as an antenna for establishing a radio frequency (RF) communication link 45 with the external programmer 44; or the coil 43 may serve as a means for inductively coupling data to/from the telemetry circuit 42 and from/to the external programmer 44 as is known in the art. See for example U.S. Pat. No. 4,809,697 (Causey, III et al.) and U.S. Pat. No. 4,9442,299 (Silvian) incorporated herein by reference in their entirety. Further, such telemetry circuit 42 advantageously allows status information relating to the operation of the ICD/pacemaker 10 as contained in the control/timing circuit 22 and/or memory 36 to be sent to the external programmer 44 through the established link 45.

The control/timing circuit 22 includes appropriate processing and logic circuits for analyzing the outputs of the sense amplifiers 26 and 24 and determining if such signals indicate the presence of an arrhythmia. Typically, the control/timing circuit 22 is based on a microprocessor or similar processing circuit, which includes the ability to process or monitor input signals (data) in a prescribed manner, e.g., as controlled by program code stored in a designated area or block of the memory circuit 36. The details of the design and operation of the control/timing circuit 22 are not critical to the present invention. Rather, any suitable control/timing circuit 22 may be used that carries out the functions described herein. The use, design and operation of microprocessor-based control circuits to perform timing and data analysis functions is well known in the art.

The ICD/pacemaker 10 additionally includes a battery 40, which provides operating power to all of the circuits of the ICD/pacemaker 10 via a power signal line 39 and a clock 41 which is used for timing the various functions of the device and which is in communication with the control/timing circuit 22. It will be appreciated by those of skill in the art that the clock 41, though illustrated as separate from the control/timing circuit, may optionally be integral thereto.

Within the control/timing circuit 22 is an activation/deactivation circuit 46 in communication with the atrial sense amplifier 26 via power control path 47. The power control path 47 preferably causes a switch, e.g., a transistor or the like, to enable and/or disable the supply of power (supplied from the battery 40 via path 39) to the atrial sense amplifier 26. In a preferred embodiment of the ICD/pacemaker 10 the activation/deactivation circuit 46 activates and/or deactivates the atrial sense amplifier 26 in response to data sensed by the ventricular 24 and/or atrial 26 sense amplifiers, and/or operation of the cardioversion-defibrillation circuit 38, and/or operation of the ventricular pulse generator 30.

As needed for certain applications, the ICD/pacemaker 10 may further include at least one sensor 48 that is connected to the control/timing circuit 22 of the ICD/pacemaker 10. As illustrated in FIG. 1, this sensor 48 is optionally included within the ICD/pacemaker 10. It will be appreciated by those of skill in the art that the sensor may also be external to the device, either implanted elsewhere within the patient or carried by the patient, or may be absent altogether. A type of sensor commonly employed in ICD/pacemakers is an activity sensor, such as a piezoelectric crystal, that is mounted to the case of the pacemaker. Other types of sensors are also known, such as sensors that sense the oxygen content of blood, respiration rate, pH of blood, body motion and the like. The presence of such a sensor is not critical to the invention and thus, the type employed, if any, is also not critical to the invention contemplated herein. Any sensor or combination of sensors capable of sensing one or more a physiological or physical parameters relatable to the rate at which the heart should be beating (i.e., relatable to the metabolic need of the patient), and/or relatable to whether a tachyarrhythmia is likely to soon occur can be used. Such sensors are commonly used with "rate-responsive" ICD/pacemakers in order to adjust the rate (pacing cycle) of the device in a manner that tracks the physiological and metabolic needs of the patient. It will be appreciated by those with skill in the art that other hardware, software, and hardware/software combinations may be included within the ICD/pacemaker device without affecting the operation or usefulness of the present invention. Thus, any pacing device designed to pace in both the atrium and ventricle of the heart is amenable for use in the present invention.

It is noted that leads 14 and 16 of FIG. 1 are illustrated as being in contact with the right ventricle and atrium, respectively, of the heart 12. As is well known to those of skill in the art, these leads may be in either the right or left atrium or the right or left ventricle. Further, as will be appreciated, the atrial lead may be positioned within the superior vena cava, rather than in either atria, in order to detect depolarization in the atrium. The positioning of the leads within the heart or near the heart may be in any manner known to those with skill in the art. However, the invention described herein is designed to operate in dual-chamber pacing devices. Therefore, at least one lead must be positioned in contact with or in proximity to at least one atrium, and at least one lead must be in contact with or in proximity to at one least ventricle, such that each and/or both chambers may be sensed and/or paged as necessary.

Furthermore, as discussed above, the control/timing circuit 22 may be realized using a variety of techniques and/or circuits. The preferred type of control/timing circuit 22 is a microprocessor-based control system. It is noted however, that the control/timing circuit 22 may also be realized using a state machine. Indeed any type of control circuit or system could be employed for the control/timing circuit 22. The present invention is thus not concerned with the details of the control/timing circuit 22; rather, it is concerned with the end result achieved by that circuit. That is, as long as the control/timing circuit 22 controls the operation of the ICD/pacemaker 10 (or similar medical device) such that the desired functions are achieved as get forth herein (e.g., as described in the flow charts of FIGS. 2–4), it matters little what type of control/timing circuit or system is used. Those of skill in the implantable medical device art, given the teachings presented herein, will be able to fashion numerous and varied types of control circuits or systems capable of achieving the desired device control.

Representative of the types of control systems that may be used with the invention is the microprocessor-based control system described in U.S. Pat. No. 4,940,052 entitled "Microprocessor Controlled Rate-Responsive Pacemaker Having Automatic Rate Response Threshold Adjustment". Reference is also made to U.S. Pat. Nos. 4,712,555 and 4,944,298, wherein a state machine type of operation is described; and U.S. Pat. No. 4,788,980 wherein the various timing intervals used within the pacemaker and their inter-relationships are more thoroughly described. Each of the '052, '555, '298 and '980 patents are incorporated herein, in their entirety, by reference.

Figure 2:
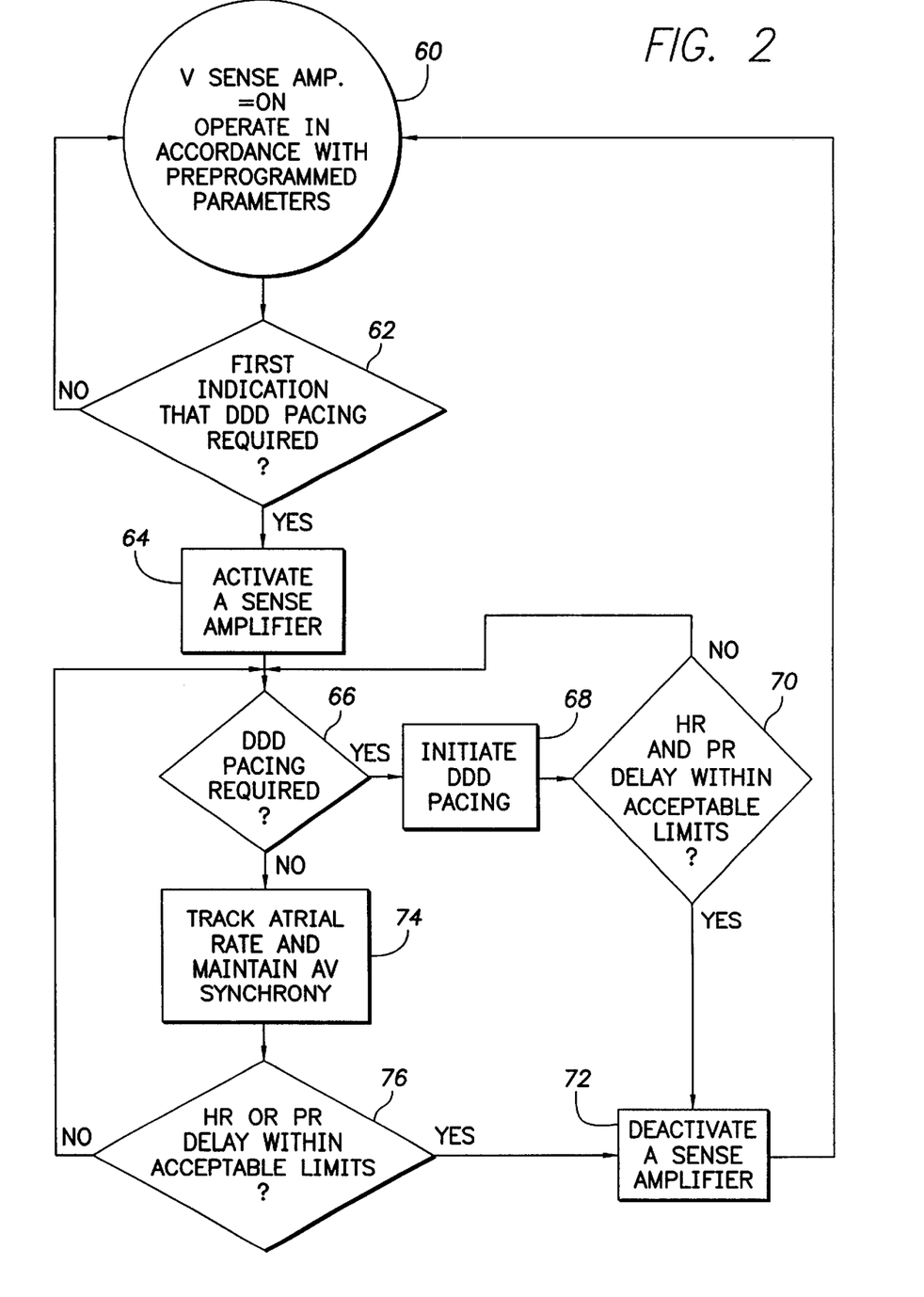
FIG. 2 is a flow chart illustrating a preferred embodiment of the improved method described herein.

Turning now to the flow chart illustrated in FIG. 2, a preferred method of operation according to the present invention is illustrated. In this flow chart as with those illustrated in FIGS. 3 and 4, each main step of the method is depicted in a "box" or "block", with each block having a reference numeral assigned thereto for reference purposes. Beginning then with block 60 of FIG. 2, the ventricular sense amplifier 24 is ON and the ICD/pacemaker 10 is operating in accordance with its preprogrammed parameters, that is, the preprogrammed cardioversion-defibrillation and pacing routines. In block 62 a first determination is made as to whether DDD pacing is required. If DDD pacing is not required (the NO branch of block 62), the system returns to block 60 and continues to operate in its preprogrammed manner of single-chamber sensing and pacing. If it is determined that DDD pacing is required (YES branch of block 62), the atrial sense amplifier 26 is activated (block 64) via power control path 47. Once the atrial sense amplifier 26 has been activated, the need for DDD pacing is confirmed (block 66), e.g., by lack of intrinsic atrial activity. If it is confirmed that DDD pacing is required (YES branch of block 66), then DDD pacing is initiated (block 68). After initiation of DDD pacing, it is determined whether the patient's heart beat is within acceptable limits (block 70). If the heart rate (HR) or PR delay are not within acceptable limits (NO branch of block 70), the system returns to determining whether or not DDD pacing is still required (block 66), and if so, DDD pacing is continued. If it is determined that the heart rate (HR) and PR delay are within acceptable limits (YES branch of block 70), then the atrial sense amplifier 26 is deactivated (block 72) via power control path 47. If, when the system attempted to confirm whether DDD pacing was required (block 66), it was determined that no such pacing was necessary (NO branch of block 66), then the atrial rate is tracked and AV synchrony is maintained (block 74). The next inquiry is whether or not the heart rate (HR) or PR delay are within acceptable limits (block 76). If the heart rate is within acceptable limits (YES branch of block 66), the atrial sense amplifier 26 is deactivated (block 72). If on the other hand, it is determined that the heart rate (HR) or PR delay are not within acceptable limits (NO branch of block 76), the system returns to determining the need for DDD pacing (block 66). Once the atrial sense amplifier 26 has been deactivated (block 72) the system returns to the starting point (block 60) with only the ventricular sense amplifier 24 ON and single-chamber sensing and pacing occurring, i.e., VVI mode.

Figure 3:
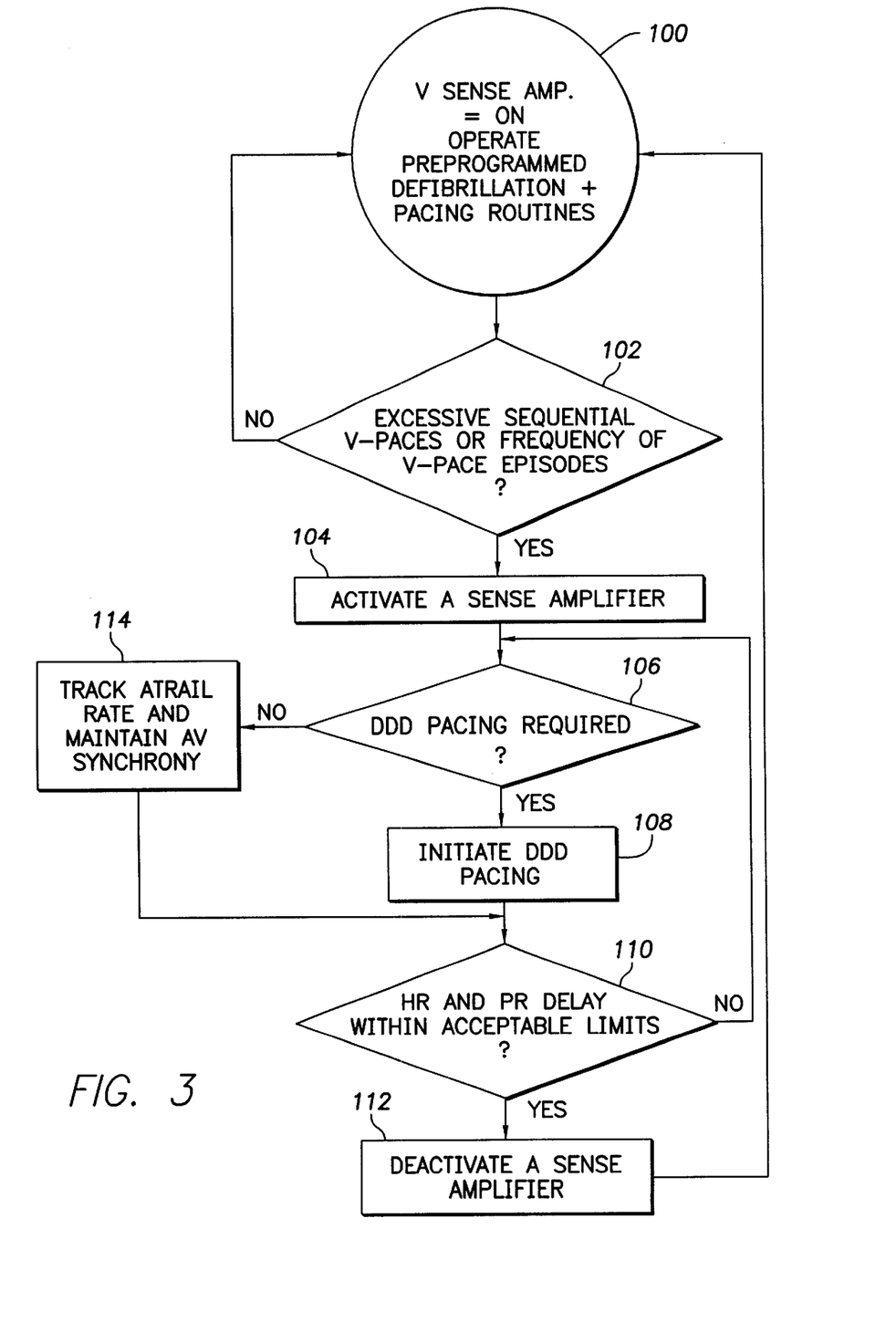
FIG. 3 is a flow chart of a preferred embodiment of the improved method described herein wherein ventricular pacing is used to determine the time for activation of the atrial sense amplifier.

Turning now to FIG. 3, a flow chart illustrating a preferred embodiment, wherein the operation of the pacing routines provides an initial indication that atrial sense amplifier activation is needed, is presented. This process begins in block 100 with the ventricular sense amplifier 24 ON and the ICD/pacemaker 10 operating in accordance with its preprogrammed single-chamber sensing and pacing routines. A first determination is made (block 102) whether an excessive frequency of ventricular pacing episodes has occurred or an excessive number of sequential ventricular paces has occurred. Those of skill in the art will appreciate that defining what is an "excessive" frequency or number of pacings may be readily determined by a physician using techniques well known in the pacing art and that such determinations are often patient-specific. Alterntively, the ICD/pacemaker 10 may be preprogrammed with defined excessive frequency and number values representative of the average numbers expected to indicate a need for dual-chamber sensing and pacing. Again such values are well known to and readily determined by those of skill in the art and will depend upon the patient's specific type of heart ailment.

Continuing with FIG. 3, if no excessive number or frequency of ventricular pacings has occurred (YES branch of block 102), then the atrial sense amplifier 26 is activated (block 104) via power control path 47. If no excessive ventricular pacing has occurred (NO branch of block 102), and thus there is no preliminary indication that DDD pacing may be necessary, the device returns to its normal operation with only the ventricular sense amplifier 24 activated. Once the atrial sense amplifier 26 is activated (block 104), the need for DDD pacing is confirmed (block 106). If it is determined that DDD pacing is not required (NO branch of block 106) (e.g., because intrinsic atrial activity is detected), then the atrial rate is tracked and AV synchrony is maintained (block 114). If, on the other hand, DDD pacing is confirmed necessary (YES branch of block 106), DDD pacing is initiated (block 108). Once the patient's heart rate (HR) and PR delay have returned to within acceptable limits (YES branch of block 110), the atrial sense amplifier 26 is deactivated (block 112) via power control path 27 and the program returns to the starting position (block 100) with only the ventricular sense amplifier 24 activated. So long as the heart rate (HR) and the PR delay of the patient is not within acceptable limits (NO branch of block 110), the ICD/pacemaker 10 continues to confirm the need for DDD pacing (block 106).

Figure 4:
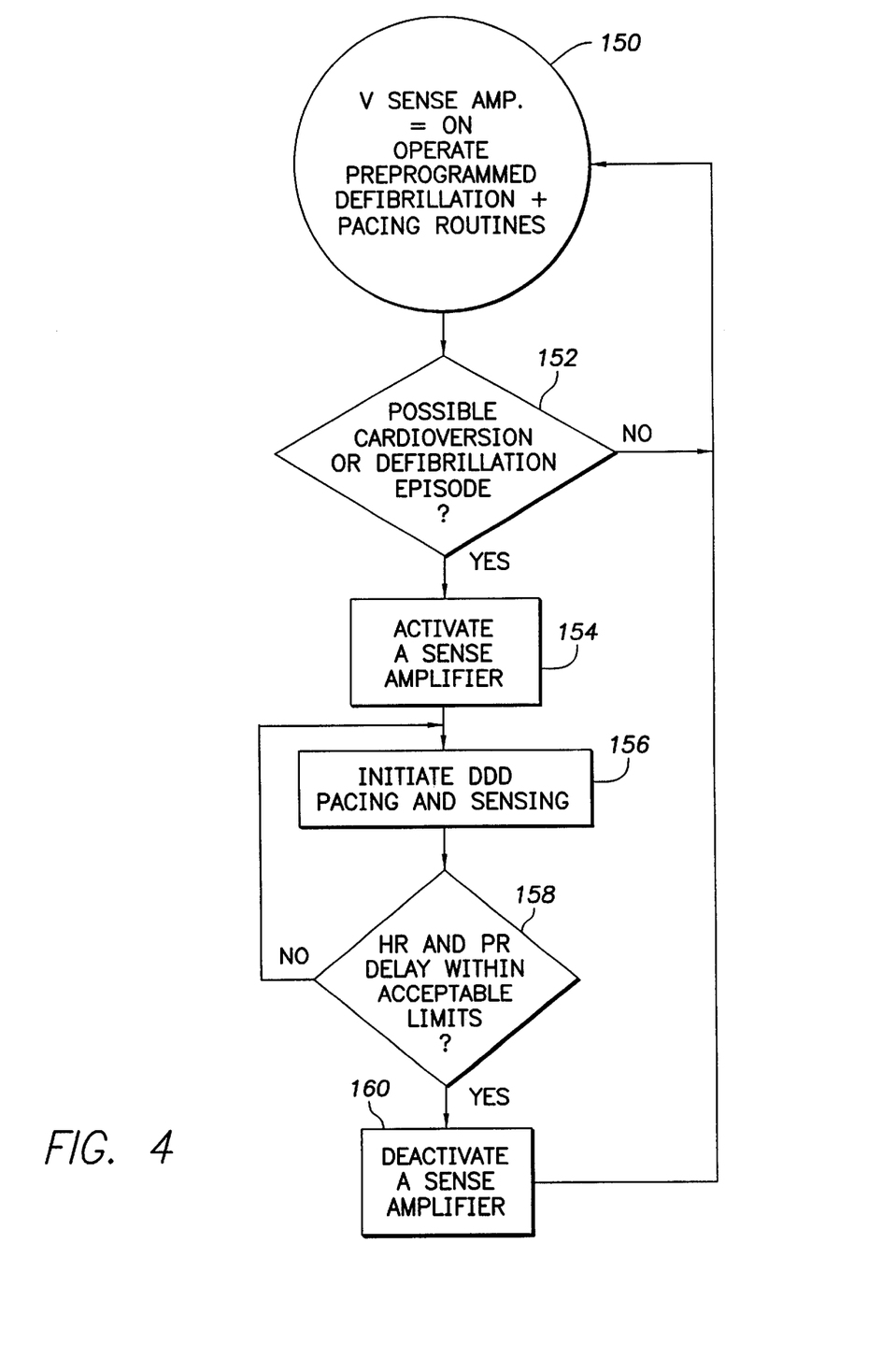
FIG. 4 is a flow chart of an alternative preferred embodiment of the improved method described herein wherein cardioversion-defibrillation events are used to determine the time for activation of the atrial sense amplifier.

FIG. 4 illustrates a preferred embodiment of the present invention wherein activation of the atrial sense amplifier 26 is triggered by the detection of ventricular arrhythmia. This process begins in block 150 with the ventricular sense amplifier 24 ON and the ICD/pacemaker 10 operating according to its preprogrammed single-chamber sensing and pacing routines. An initial determination is made as to whether either cardioversion or defibrillation episode has been detected (block 152). If no cardioversion or defibrillation episode has been detected by the ICD/pacemaker 10 (NO branch of block 152), the ICD/pacemaker 10 returns to the starting point (block 150). If a cardioversion and/or defibrillation episode has been detected by the ICD/pacemaker 10 (YES branch of block 152), the atrial sense amplifier 26 is activated (block 154) and DDD pacing and sensing is, preferably, automatically initiated (block 156).

Next, it is determined whether the heart rate (HR) and PR delay are within acceptable limits (block 158). If the heart rate (HR) and PR delay are not within acceptable limits (NO branch of block 158), DDD pacing/sensing is continued (block 156). If it is determined that the patient's heart rate (HR) and PR delay are within acceptable limits (YES branch of block 158), the atrial sense amplifier 26 is deactivated (block 160) via power control path 27 and the program returns to its starting point (block 150) with only the ventricular sense amplifier 24 ON and the preprogrammed routines operating.

While the invention herein disclosed has been described by means of specific embodiments and applications thereof, numerous modifications and variations may be made thereto by those skilled in the art without departing from the scope of the invention which is set forth in the claims. For example, while power control of the atrial sense amplifier has been expressly shown associated with the current ICD/pacemaker mode of operation, one of ordinary skill would also recognize that power control could also be extended to control other portions of the circuitry of the ICD/pacemaker, e.g., the atrial and/or ventricle pulse generators, that are not needed in a particular operating mode.

What is claimed is:

1. In an implantable ICD/pacemaker, having DDD pacing capabilities and having an atrial sense amplifier, a ventricular sense amplifier, a ventricular pulse generator, an atrial pulse generator, a control/timing circuit, an activation/deactivation circuit for activating and deactivating the atrial sense amplifier, cardioversion-defibrillation circuitry, and a memory circuit, wherein the atrial sense amplifier is initially in a deactivated state, a method of operation for reducing power consumption of the ICD/pacemaker comprising the steps of:

sensing an arrhythmia with the ventricular sense amplifier;

providing therapy to correct the arrhythmia, wherein the therapy is selected from the group consisting of ventricular pacing, cardioversion and defibrillation;

activating the atrial sense amplifier in response to a predefined event, wherein the predefined event is selected from the group consisting of detecting a ventricular pacing rate greater than a predetermined amount, detecting a sequential number of ventricular paces greater than a predetermined number, and detection of ventricular arrhythmia;

sensing heart activity with the atrial sense amplifier and ventricular sense amplifier; and deactivating the atrial sense amplifier when the heart activity is within predefined acceptable limits, thereby reducing the power consumption of the implantable ICD/pacemaker.

2. The method of claim 1, further comprising initiating DDD pacing and sensing following activation of the atrial sense amplifier in response to a predefined event selected from the group consisting of detection of ventricular arrhythmia or tachycardia.

3. The method of claim 1, further comprising confirming the need for DDD pacing after activating the atrial sense amplifier and initiating atrial sensing.

4. The method of claim 3, further comprising recording in the memory circuit the frequency and type of therapy provided including recording sequential ventricular pacing events and frequency of ventricular pacing events that exceed predetermined limits.

* * * * *